(12) United States Patent
Silverman

(10) Patent No.: US 7,938,849 B2
(45) Date of Patent: May 10, 2011

(54) METHOD FOR TREATING LONG BONE FRACTURES

(76) Inventor: Barry J. Silverman, Aventura, FL (US)

( * ) Notice: Subject to any disclaimer, the term of this patent is extended or adjusted under 35 U.S.C. 154(b) by 1333 days.

(21) Appl. No.: 11/424,070

(22) Filed: Jun. 14, 2006

(65) Prior Publication Data

US 2006/0235406 A1    Oct. 19, 2006

Related U.S. Application Data

(63) Continuation of application No. 10/620,919, filed on Jul. 16, 2003, now Pat. No. 7,070,600.

(51) Int. Cl.
*A61B 17/88* (2006.01)

(52) U.S. Cl. .......................... 606/281; 606/71

(58) Field of Classification Search .................. 606/280, 606/70, 71, 281, 286, 74
See application file for complete search history.

(56) References Cited

U.S. PATENT DOCUMENTS

| | | | |
|---|---|---|---|
| 1,950,799 A | 3/1934 | Jones | |
| 2,825,329 A | 3/1958 | Caesar | |
| 3,593,709 A | 7/1971 | Halloran | |
| 3,693,616 A | 9/1972 | Roaf et al. | |
| 4,905,679 A | 3/1990 | Morgan | |
| 5,000,166 A | 3/1991 | Karpf | |
| 5,084,049 A | 1/1992 | Asher et al. | |
| 5,092,893 A | 3/1992 | Smith | |
| 5,190,545 A * | 3/1993 | Corsi et al. | 606/74 |
| 5,527,310 A | 6/1996 | Cole et al. | |
| 5,665,089 A * | 9/1997 | Dall et al. | 606/71 |
| 5,702,399 A | 12/1997 | Kilpela et al. | |
| 5,707,372 A | 1/1998 | Errico et al. | |
| 5,718,705 A | 2/1998 | Sammarco | |
| 5,728,097 A | 3/1998 | Mathews | |
| 5,752,955 A | 5/1998 | Errico | |
| 5,980,523 A | 11/1999 | Jackson | |
| 5,993,452 A * | 11/1999 | Vandewalle | 606/74 |
| 6,228,087 B1 | 5/2001 | Fenaroli et al. | |
| 6,348,052 B1 | 2/2002 | Sammarco | |
| 6,355,036 B1 | 3/2002 | Nakajima | |
| 6,361,538 B1 | 3/2002 | Fenaroli et al. | |
| 6,379,359 B1 | 4/2002 | Dahners | |
| 6,432,108 B1 | 8/2002 | Burgess et al. | |
| 6,488,685 B1 | 12/2002 | Manderson | |
| 6,520,965 B2 * | 2/2003 | Chervitz et al. | 606/74 |
| 2002/0032444 A1 | 3/2002 | Mische | |
| 2004/0117016 A1 | 6/2004 | Abramson | |

FOREIGN PATENT DOCUMENTS

EP    0 362 049 A1    9/1989

* cited by examiner

*Primary Examiner* — Thomas C Barrett
*Assistant Examiner* — Michael J Araj
(74) *Attorney, Agent, or Firm* — Fleit Gibbons Gutman Bongini & Bianco, PL; Paul D. Bianco; Martin Fleit

(57) ABSTRACT

A method is provided for treating a fractured long bone. The method includes fastening a first bone plate to cortical bone of the fractured long bone and fastening a second bone plate to cortical bone of the fractured long bone. The first bone plate is circumferentially spaced from the second bone plate. The method also includes fastening a first end of a transverse member to the first bone plate and fastening a second end of the transverse member to the second bone plate.

5 Claims, 4 Drawing Sheets

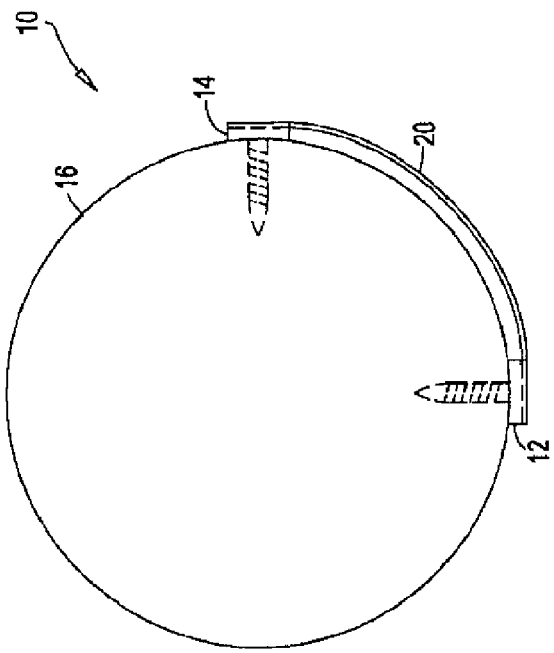
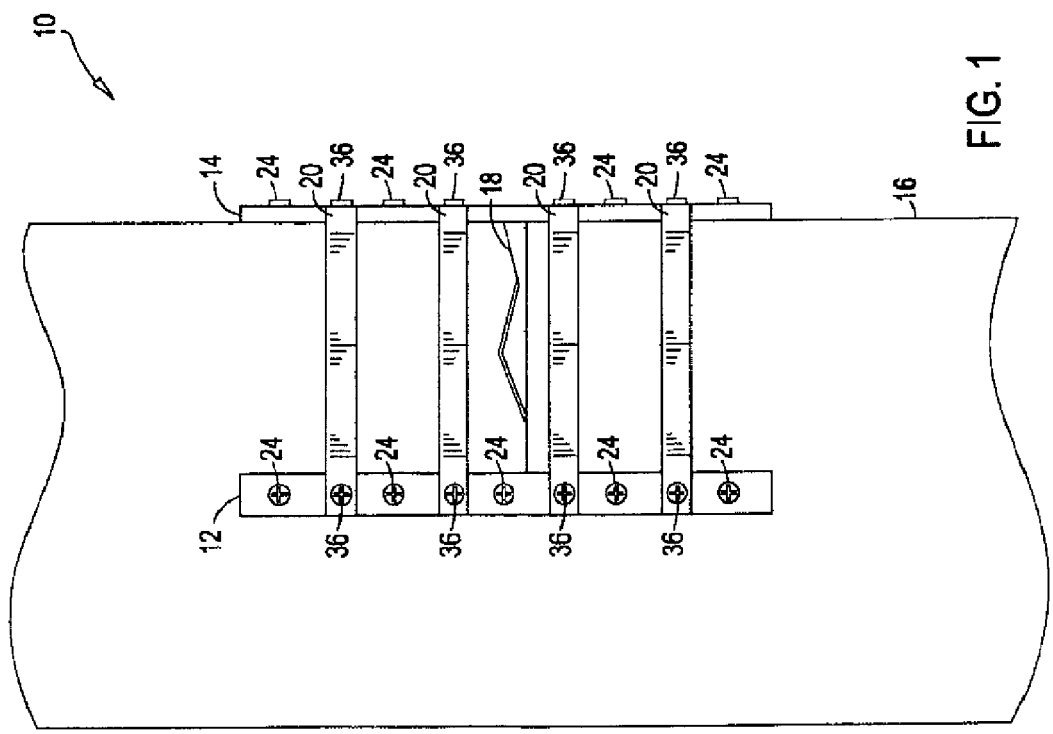

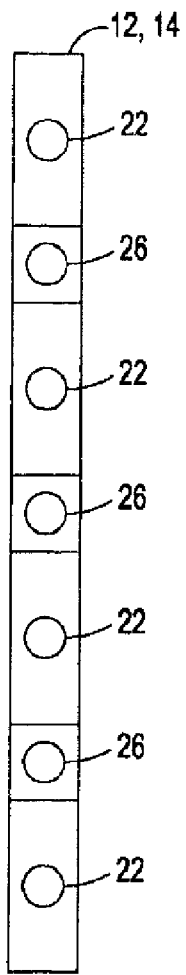
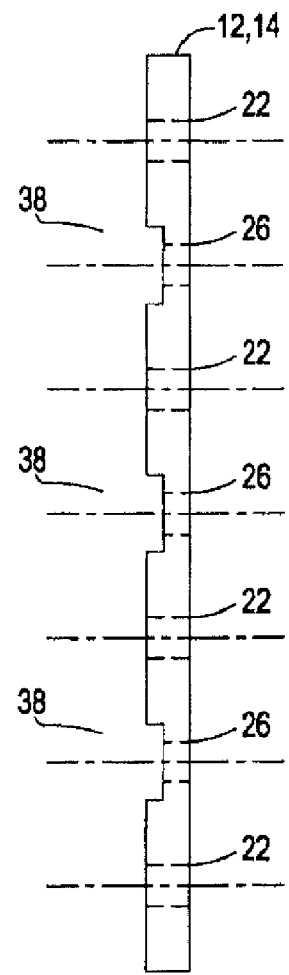
FIG. 3                    FIG. 4
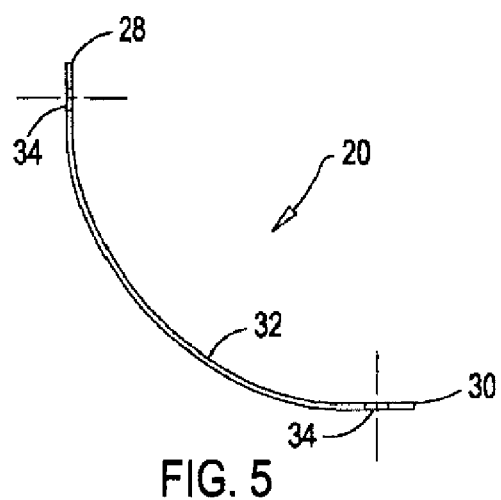
FIG. 5

METHOD FOR TREATING LONG BONE FRACTURES

CROSS-REFERENCE TO RELATED APPLICATION

This application is a continuation of U.S. patent application Ser. No. 10/620,919 filed Jul. 16, 2003, now U.S. Pat. No. 7,070,600 the contents of which are incorporated by reference in their entirety.

FIELD OF THE INVENTION

The present invention relates generally to a method and device for the treatment of orthopedic fractures, and more particularly, to the internal fixation of long bone fractures.

BACKGROUND OF THE INVENTION

The repair of fractured long bones may be accomplished by the attachment of bone plates to the injured bone to hold the opposing fractured sides of the bone in place during healing. Bone plates are generally described as devices with at least one flattened surface and with holes or grooves for screws and/or wires situated in or along the main body of the plate, to allow fixation of the flattened surface of the device to the bone surface. The fixation of the bone plate is intended to hold the bone in place and achieve union of the bone fragments.

In the treatment of long bone fracture, the bone plate is rigidly affixed along the longitudinal length of the long bone to prevent motion between the fragments. For example, as shown in U.S. Pat. No. 5,702,399 to Kilpela et al., a bone plate is secured to a bone by cables looped around the bone.

Upon installation, the external forces applied to the bone plate are not limited to one particular plane and there may be simultaneous forces in several planes. Thus, a plate which is usually flattened on one or more surfaces will not bear loads equally in all directions and may be adequate to withstand forces in one direction but inadequate to withstand forces in another. For example, a bone plate can adequately withstand compressive and tensile forces along its longitudinal length, substantially preventing movement of the bone fracture. However, a bone plate can be inadequate in withstanding torsional forces, allowing movement of the bone fracture under such loading.

There therefore exists a need for an improved method and device for long bone fracture fixation.

SUMMARY OF THE INVENTION

The present invention provides a device for the treatment of long bone fractures. The device is affixable to the long bone, providing structural stability to the long bone and the bone fracture. Upon fixation to the long bone, the device substantial prevents movement of the bone fracture when the long bone is subjected to compressive, tensile, or bending forces. Additionally, the device substantially prevents movement of the bone fracture when the long bone is subjected to torsional forces.

The device includes a plurality of bone plates affixable to the cortical surface of a long bone, wherein the bone plates provide longitudinal stability to the long bone and the bone fracture. At least one of the bone plates can be affixed to the lateral side of the bone to increase the bone fracture stability when the bone is subjected to bending forces. Additionally, at least one transverse member is affixable to and interposed between the plurality of bone plates, wherein the transverse members provide torsional stability to the long bone and the bone fracture.

The bone plates are affixed to the cortical surface of the long bone along a longitudinal length of the long bone. The bone plates each include a plurality of screw holes extending therethrough for receiving a bone screw. The bone plates are affixed to the bone by passing a bone screw through the screw holes and screwing into the bone. Alternatively, other known means or mechanisms can be used to attach the plates to the bone.

In one embodiment, the bone plates further include a plurality of threaded holes extending therethrough, for the attachment of the transverse members. The transverse members each include a first end and a second end, the first end and the second end each having a screw hole therethrough for receiving a transverse member attachment screw. The transverse members are attached to the bone plates by screwing the transverse member attachment screw into the threaded holes of the bone plates.

BRIEF DESCRIPTION OF THE DRAWINGS

A more complete understanding of the present invention, and advantages and features thereof, will be more readily understood by reference to the following detailed description when considered in conjunction with the accompanying drawings wherein:

FIG. 1 is a front view of a long bone segment including the device of the present invention;

FIG. 2 is a top view of a long bone segment including the device of the present invention;

FIG. 3 is a front view of an exemplary bone plate of the device of the present invention;

FIG. 4 is a side view of an exemplary bone plate of the device of the present invention;

FIG. 5 is a top view of a transverse member of the device of the present invention;

DETAILED DESCRIPTION OF THE INVENTION

Figure 6:
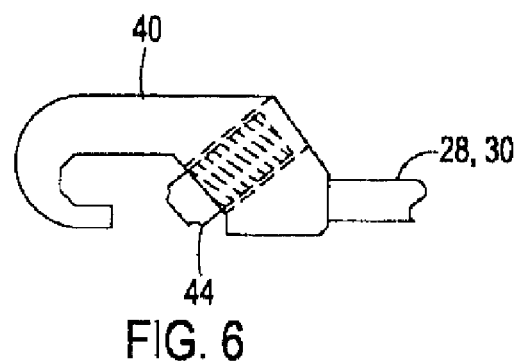
FIG. 6 is a sectional view of an end of a transverse member of the device of the present invention.

The present invention provides a device for the treatment of long bone fractures. The device is affixable to the long bone, providing structural stability to the long bone and the bone fracture. Upon fixation to the long bone, the device substantial prevents movement of the bone fracture when the long bone is subjected to compressive, tensile or bending forces. Additionally, the device substantially prevents movement of the bone fracture when the long bone is subjected to torsional forces.

Referring now to the figures in which like reference numerals refer to like elements, there is shown in FIGS. 1 and 2 the device 10 of the present invention. The device 10 includes a first bone plate 12 and a second bone plate 14, each affixable to the cortical surface of a long bone 16. The bone plates 12 and 14 are affixed along the longitudinal length and about the circumference of the long bone 16, wherein the bone plates 12 and 14 intersect a bone fracture 18. The bone plates 12 and 14 substantially prevent movement of the bone fracture 18 when the long bone 16 is subjected to compressive and tensile forces. Additionally, at least one of the bone plates 12 or 14 can be affixed to a lateral side of the long bone 16 to substantially prevent movement of the long bone fracture 18 when the long bone 16 is subjected to bending forces.

FIG. 1 shows an anterior-posterior view of bone 16 and FIG. 2 shows a cephalad-caudal view of bone 16. It should be understood that the surgeon or other medical practitioner utilizing device 10 can position device 10 in any desired fashion based on a number of factors such as the location and type of bone fracture 18. Although the bone fracture 18 is shown as a simple fracture, device 10 can be used with all types of fractures. Furthermore, device 10 can be used for other procedures (e.g. osteotomy or allograph replacement) or situations in which stability of a long bone is desired. Device 10 can be made of any suitable material typically used in orthopedic applications (metals and alloys, ceramics, polymers, either resorbable or not, and composites). Examples of metallic materials include titanium, a titanium alloy, or stainless steel. If device 10 is made of a metallic material, the same metallic material can be used for all of the components to avoid galvanic (mixed-metal) corrosion.

The device 10 further includes at least one transverse member 20 affixable to the bone plates 12 and 14. The transverse members 20 are affixed to and interposed between the first bone plate 12 and the second bone plate 14. The transverse members 20 substantially prevent movement of the bone fracture 18 when the long bone 16 is subjected to torsional forces.

Referring to FIGS. 3 and 4, the bone plates 12 and 14 each include a plurality of screw holes 22, extending therethrough for receiving bone screws 24 to be driven into the long bone 16. (See also FIG. 1). The bone screws 24 can be driven into the long bone 16 at orthogonal or oblique angles to the surface of the long bone 16. The screw holes 22 can have any configuration. For example and as is well known, the screw holes 22 can be configured and dimensioned to achieve compression of the fracture as the bone screws 24 are inserted into the long bone 16. Also, the screw holes 22 and the heads of the screws 24 can be threaded so that locking of the screws 24 to the plates 12 and 14 is achieved. If desired, a combination of the compression and locking screw holes 22 can be used. Furthermore, the present invention also envisions other mechanisms (e.g. cerclage) for attaching the bone plates 12 and 14 to the long bone 16.

The bone plates 12 and 14 also can include a second series of holes used to connect with the transverse members 20. Specifically, the bone plates 12 and 14 each include a plurality of threaded holes 26 extending therethrough for attachment of the transverse members 20.

Referring to FIG. 5, the transverse members 20 each include a first end 28, a second end 30, and an intermediate section 32 therebetween that partially spans the circumference of the long bone 16. Transverse members 20 can be manufactured to have a curvature and/or can be bent by the surgeon to custom shape for an individual patient. The first end 28 and the second end 30 each has a screw hole 34 therethrough for receiving a transverse member attachment screw 36. A transverse member 20 is affixed to the bone plates 12 and 14 by passing the transverse member attachment screw 36 through the screw hole 34 and engaging the threaded holes 26 on the bone plates 12 and 14. (See also FIG. 1) At least one of transverse member 20 is affixed to adjacent bone plates 12 and 14, wherein the transverse member 20 span the radial distance between the bone plates 12 and 14, providing torsional support to the device 10.

The attachment screws 36 can be bone screws which are driven into the long bone 16. Additionally, the transverse member screw holes 34 can be unthreaded screw holes, configured for receiving bone screws 24, which are driven into the long bone 16.

Referring again to FIG. 4, the bone plates 12 and 14 include a plurality of notched segments 38. The notched segments 30 are located along the length of the bones plate 12 and 14, such that a threaded hole 26 is positioned within each of the notched segments 38. The notched segments 38 are configured for receiving the first end 28 and the second end 30 of the transverse members 20, such that the first end 28 and the second end 30 of the transverse members 20 are recessed within the bone plates 12 and 14. The notched segments 38 reduce the overall profile of the device 10, allowing the transverse member 20 to be substantially flush with the top surface of the bone plates 12 and 14.

Figure 7:
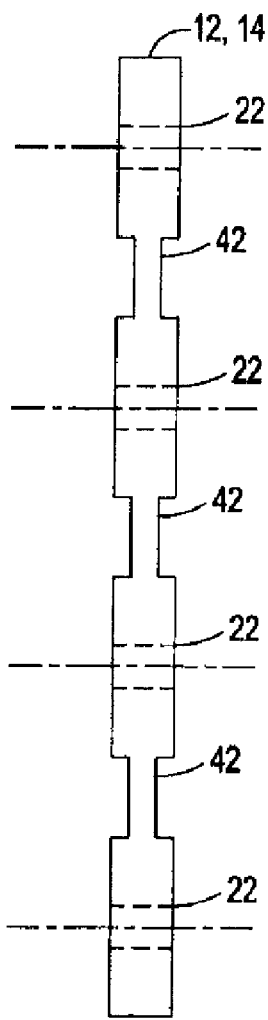
FIG. 7 is a side view of a bone plate of the device of the present invention including notched segments for attachment of the hook member of FIG. 6.

Referring to FIGS. 6 and 7, the first end 28 and the second end 30 of the transverse members 20 each include a hook member 40 for engaging the bone plates 12 and 14. The bone plates 12 and 14 each include a plurality of screw holes 22, extending therethrough for receiving bone screws 24 to be driven into the long bone 16. (See also FIG. 1). Notched segments 42 are located between the screw holes 22, wherein the hook members 40 engage the notched segment 42. The hook members 40 each include a set screw 44 for securing the transverse member 20 to the bone plates 12 and 14, wherein the set screw compressably engages the notched segment 42 thereby securing the hook member 40 to the bone plate 12 or 14.

In an alternative embodiment the set screw 44 also engages the long bone 16. The set screw 44 is driven obliquely into the long bone 16 securing the hook member 40 to the long bone 16 and to the bone plate notched segment 42.

Figure 8:
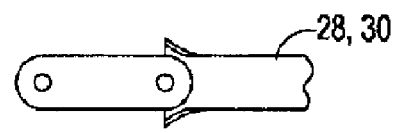
FIG. 8 is a sectional view of a transverse member of the device of the present invention.

Referring to FIG. 8, the first end 28 and the second end 30 of the transverse member are pivotally connected to the transverse member 20. The pivotal connection has a limited range of motion, maintaining torsional stability of the device 10. In the instance where the bone plates 12 and 14 are not aligned along the longitudinal length of the long bone 16, the pivotably connected first end 28 and second end 30 allow the transverse members 20 to be affixed to the bone plates 12 and 14 without adjusting the position of the bone plates 12 and 14. Exemplary embodiments of transverse members 20 including pivotable ends are provided in U.S. Pat. No. 5,707,372 to Errico et al. and U.S. Pat. No. 5,980,523 to Jackson, which are herein incorporated by reference.

Figure 9A:
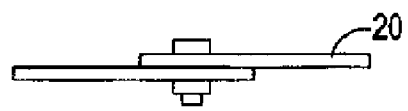
FIGS. 9a and 9b is an adjustable length transverse member of the device of the present invention.
Figure 9B:
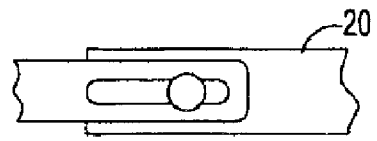

Referring to FIGS. 9a-b, the transverse members 20 are adjustable. In the instances where the distance between adjacent bone plates 12 and 14 is not consistent along the longitudinal length of the long bone 16, the adjustable length of the transverse members 20 allows the transverse members 20 to be affixed to the bone plates 12 and 14 without adjusting the position of the bone plates 12 and 14. Exemplary embodiments of adjustable length transverse members 20 are provided in U.S. Pat. No. 6,432,108 to Burgess et al and U.S. Pat. No. 5,752,955 to Errico, which are herein incorporated by reference.

Figure 10:
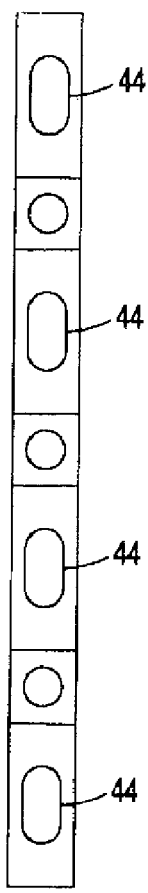
FIG. 10 is a front view of a bone plate of the device of the present invention including elongated screw holes.

Referring to FIG. 10, the bone plates 12 and 14 each include a plurality of elongated screw holes 44, extending there through for receiving bone screws 24 to be driven into the long bone 16. In the instance where the bone plates 12 and 14 are not aligned along the longitudinal length of the long bone 16, the elongated screw holes 44 allow the position of the bone plates 12 and 14 to be adjusted to align the bone plates 12 and 14 for attachment of the transverse members 20.

In an exemplary embodiment, the bone plates 12 and 14 are semi-rigid, having a malleable conformation, such that the bone plates 12 and 14 can conform to the surface of the long bone 16. Semi-rigid is defined as meaning that the bone plates 12 and 14 are conformable to the surface of the long bone 16, yet the bone plates 12 and 14 retain sufficient rigidity to provide structural stability to the long bone 16 under compressive, tensile, and bending forces.

Additionally, the bone plates 12 and 14 can be of different sizes. For example, when a first bone plate 12 is affixed to a lateral side of the long bone 16 and the second bone plate 14 is affixed to either the posterior or anterior side of the long bone 16, the second bone plate can have a thickness less than the thickness of the first bone plate 12.

Figure 11:
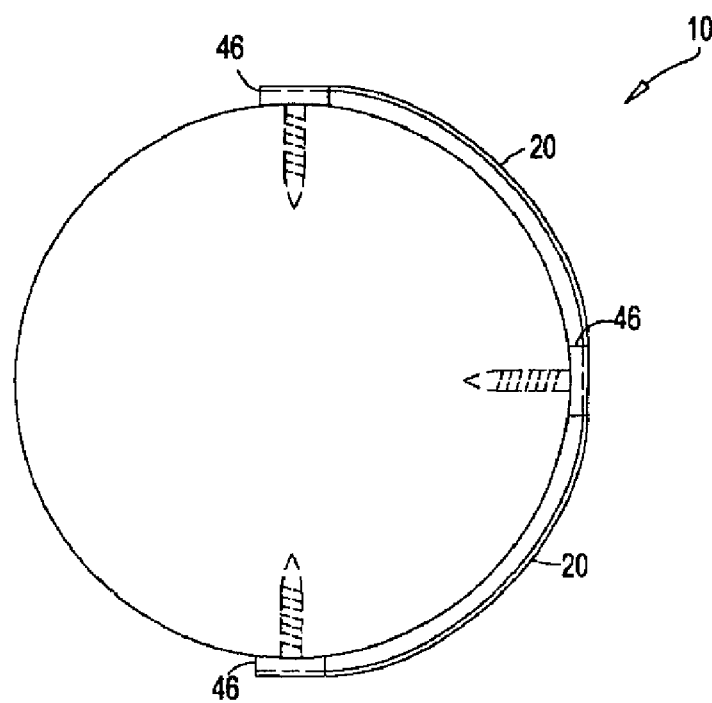
FIG. 11 is a top view of a long bone segment including the device of the present invention having a plurality of bone plates.

Referring to FIG. 11, which shows a cephalad-caudal view, the device 10 of the present invention includes a plurality of bone plate 46. The bone plates 46 are affixable to the cortical surface of a long bone 16 along a longitudinal length of the long bone 16. The transverse members 20 are connected to and interposed between adjacent bone plates 46, providing torsional stability to the device 10.

In an exemplary method of use, the device 10 of the present invention is affixed to the femur to treat an orthopedic fracture. Initially, access is gained to the treatment site using procedures and instrumentation known in the art. For example, percutaneous and other minimally invasive procedures can be used. The first bone plate 12 is affixed to the cortical surface of the femur by inserting the bone screws 24 through the screw holes 22 and screwing into the femur. The first bone plate 12 is affixed to the lateral side of the femur along the longitudinal length of the femur and intersecting the bone fracture 18. The second bone plate 14 is affixed to the cortical surface of the femur in similar fashion as the first bone plate 12, wherein the second bone plate 14 is circumferentially offset from and substantially parallel to the first bone plate 12. The first bone plate 12 and the second bone plate 14 substantially prevent movement of the bone fracture 18 when the femur is subjected to compressive and tensile forces.

The transverse members 20 are connected to the first bone plate 12 and the second bone plate 14, wherein the transverse members 20 are affixed to the bone plates 12 and 14 by passing the transverse member attachment screws 36 through the screw hole 34 and engaging the threaded holes 26 on the bone plates 12 and 14. For example, a first end 28 of a transverse member 20 is aligned with a threaded hole 26 on the first bone plate 12 and second end 30 of the transverse member 20 is aligned with the corresponding threaded hole 26 on the second bone plate 14. Transverse member attachment screws 36 are passed through the screw holes 34 and threaded into the threaded holes 26 on both bone plates 12 and 14, securing the transverse member 20 to the bone plates 12 and 14. This is repeated for each of the transverse members 20, until all transverse members 20 are installed. The transverse members 20 span the radial distance between the bone plates 12 and 14, providing torsional support to the device 10.

While various descriptions of the present invention are described above, it should be understood that the various features could be used singly or in any combination thereof. Therefore, this invention is not to be limited to only the specifically preferred embodiments depicted herein.

Further, it should be understood that variations and modifications within the spirit and scope of the invention might occur to those skilled in the art to which the invention pertains. Accordingly, all expedient modifications readily attainable by one versed in the art from the disclosure set forth herein that are within the scope and spirit of the present invention are to be included as further embodiments of the present invention. The scope of the present invention is accordingly defined as set forth in the appended claims.

What is claimed is:

1. A method for treating a fractured long bone, the method comprising:
   fastening a plurality of bone plates to cortical surfaces of the fractured long bone, the plurality of bone plates circumferentially spaced apart from each other; and
   fastening a plurality of arcuate transverse members to the plurality of bone plates, the plurality of transverse members fastened to the plurality of bone plates with a plurality of attachment screws,
   wherein fastening the plurality of arcuate transverse members to the plurality of bone plates includes, for each transverse member, fastening a first end of the transverse member to one bone plate and a second end of the transverse member to a different bone plate;
   wherein the plurality of transverse members substantially prevents a torsional movement of the long bone fracture; and
   wherein each bone plate includes a plurality of notched segments and wherein fastening the plurality of transverse members to the plurality of bone plates includes positioning the plurality of transverse members in the plurality of notched segments, such that the first and second ends of each transverse member are recessed within the bone plates and are substantially flush with a top surface of the bone plates.

2. The method of claim 1 wherein the first bone plate is conformable to the cortical bone of the fractured long bone.

3. The method of claim 1 wherein the plurality of bone plates is aligned generally parallel to the long axis of the fractured long bone.

4. The method of claim 1 wherein the plurality of bone plates substantially prevents a longitudinal movement of the long bone fracture.

5. The method of claim 1 wherein fastening the plurality of transverse members to the plurality of bone plates includes positioning the attachment screws into threaded holes in the bone plates.

* * * * *